US00PP37337P2

(12) United States Plant Patent
Grazzini et al.

(10) Patent No.: US PP37,337 P2
(45) Date of Patent: Mar. 17, 2026

(54) HYBRID LAVENDER PLANT NAMED 'SENS-M1'

(50) Latin Name: ***Lavandula* x *intermedia***
Varietal Denomination: SENS-M1

(71) Applicants: Richard A. Grazzini, Columbus, OH (US); Lloyd Traven, Kintnersville, PA (US)

(72) Inventors: Richard A. Grazzini, Columbus, OH (US); Lloyd Traven, Kintnersville, PA (US)

(73) Assignee: B & S Plants LLC, Kintnersville, PA (US)

( * ) Notice: Subject to any disclaimer, the term of this patent is extended or adjusted under 35 U.S.C. 154(b) by 0 days.

(21) Appl. No.: 19/208,197

(22) Filed: May 14, 2025

(51) Int. Cl.
*A01H 5/02* (2018.01)

(52) U.S. Cl.
USPC ..... Plt./445

(58) Field of Classification Search
USPC ..... Plt./445
CPC . A01H 5/02; A01H 5/00; A01H 6/502; A01H 6/50
See application file for complete search history.

(56) References Cited

U.S. PATENT DOCUMENTS

PP24,193 P2 * 1/2014 Traven ..... A01H 5/02 Plt./226
PP35,846 P2 * 5/2024 Carr ..... Plt./445

OTHER PUBLICATIONS

NC State Extension, North Carolina Extension Gardener Plant Toolbox, retrieved on Jul. 1, 2025 at https://plants.ces.ncsu.edu/plants/lavandula-x-intermedia/, 6 pp. (Year: 2025).*

* cited by examiner

*Primary Examiner* — June Hwu

(57) ABSTRACT

A new and distinct cultivar of *Lavandula* x *intermedia* plant named 'SENS-M1' is disclosed, characterized by white flowers held on stiff, thick, very densely flowering stems. Plants are very compact and strongly upright. Flower stems are very thick and branched, resulting in rebloom for a longer blooming season. The fragrance is strong and more floral than herbal/pungent. Tolerance for leafspot and root disease has been observed. The new cultivar is a *Lavandula* x *intermedia*, normally used for outdoor ornamental purposes.

2 Drawing Sheets

Figure 1:
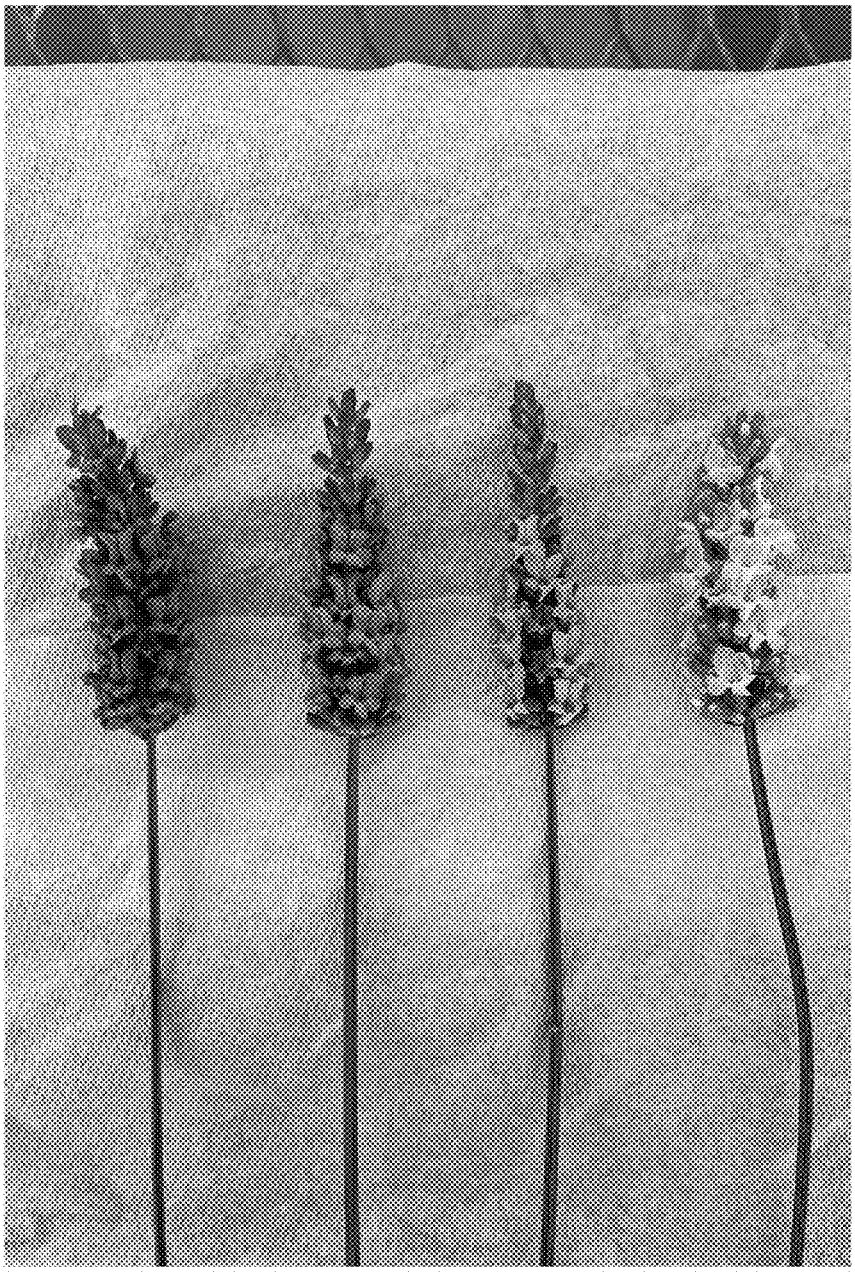

Latin name of the genus and species: *Lavandula* x *intermedia*.

Cultivar denomination: 'SENS-M1'.

BACKGROUND OF THE INVENTION

The new cultivar is a product of a planned breeding program conducted by the inventors in Bellefonte, PA. The objective of the breeding program was to produce new Lavender cultivars for ornamental commercial applications. The induced mutation resulting in this new cultivar was made during the Winter of 2020.

The parent cultivar is *Lavandula* 'TESSERACT', U.S. Plant Pat. No. 31,786. Young plants of 'TESSERACT' were treated with gamma radiation. The new cultivar was selected in July of 2019 by the inventor in a group of young plants which had been treated with induced mutation. Selection of 'SENS-M1' was made in June of 2021 when the first flowers were observed.

Asexual reproduction of the new cultivar was performed by vegetative terminal cuttings. This was first performed at a research greenhouse in Bellefonte, PA Jun. 30, 2021 and has shown that the unique features of this cultivar are stable and reproduced true to type in at least 10 successive generations.

SUMMARY OF THE INVENTION

The cultivar 'SENS-M1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SENS-M1' These characteristics in combination distinguish 'SENS-M1' as a new and distinct *Lavandula* cultivar:

1. White flower petals.
2. Broad, bright silver foliage with thick substance.
3. Very compact and strongly upright plant habit.
4. Large flowers on very densely flowering spikes.
5. Flower stems that are very thick and branched, resulting in rebloom for a longer blooming season.
6. Exhibits tolerance to leaf spotting and root disease.
7. Strong, pleasant lavender fragrance that is more floral than herbal.

PARENTAL COMPARISON

The new cultivar has white flowers. Flowers of the parent cultivar are a saturated blue. All other horticultural characteristics are identical.

COMMERCIAL COMPARISONS

Plants of the new cultivar 'SENS-M1' are comparable to the cultivar *Lavandula* 'Niko', U.S. Plant Pat. No. 24,193. The two *Lavandula* cultivars are similar in most horticultural characteristics; however, the new cultivar 'SENS-M1' differs in the following:

1. Plants of 'SENS-M1' are more compact, than the more aggressive and open in habit of 'Niko'.
2. Leaves of new cultivar are broader and thicker
3. Flower stems of new cultivar are much heavier and stiffer than flower stems of this comparator.
4. Foliage of the new cultivar is brighter silver than foliage of this comparator.
5. Flowers of the new cultivar are white; flowers of this comparator are blue.

Plants of the new cultivar 'SENS-M1' can also be compared to the commercial cultivar *Lavandula* 'Grosso', unpatented. These cultivars are similar in most horticultural characteristics however, the new cultivar 'SENS-M1' differs in the following:

1. 'SENS-M1' has a compact, branched habit, the plant habit of 'Grosso' is open, loose, and tends to lodge open.
2. 'SENS-M1' has broad and thick foliage; 'Grosso' has thin foliage.
3. 'SENS-M1' has extremely strong stems which often branch secondarily; 'Grosso' has thin and longer, weaker stems.
4. 'SENS-M1' has bright silver pubescent foliage; 'Grosso' has light gray color with thin leaves
5. 'SENS-M1' is white flowered with dense and thick flowers; 'Grosso' has light blue flowers and a thin inflorescence.

BRIEF DESCRIPTION OF THE PHOTOGRAPHS

The accompanying photograph in FIG. 1 illustrates a comparison of the of the inflorescences of the parent cultivar (3 inflorescences on the left) and the inflorescence of the new cultivar (far right).

Figure 2:
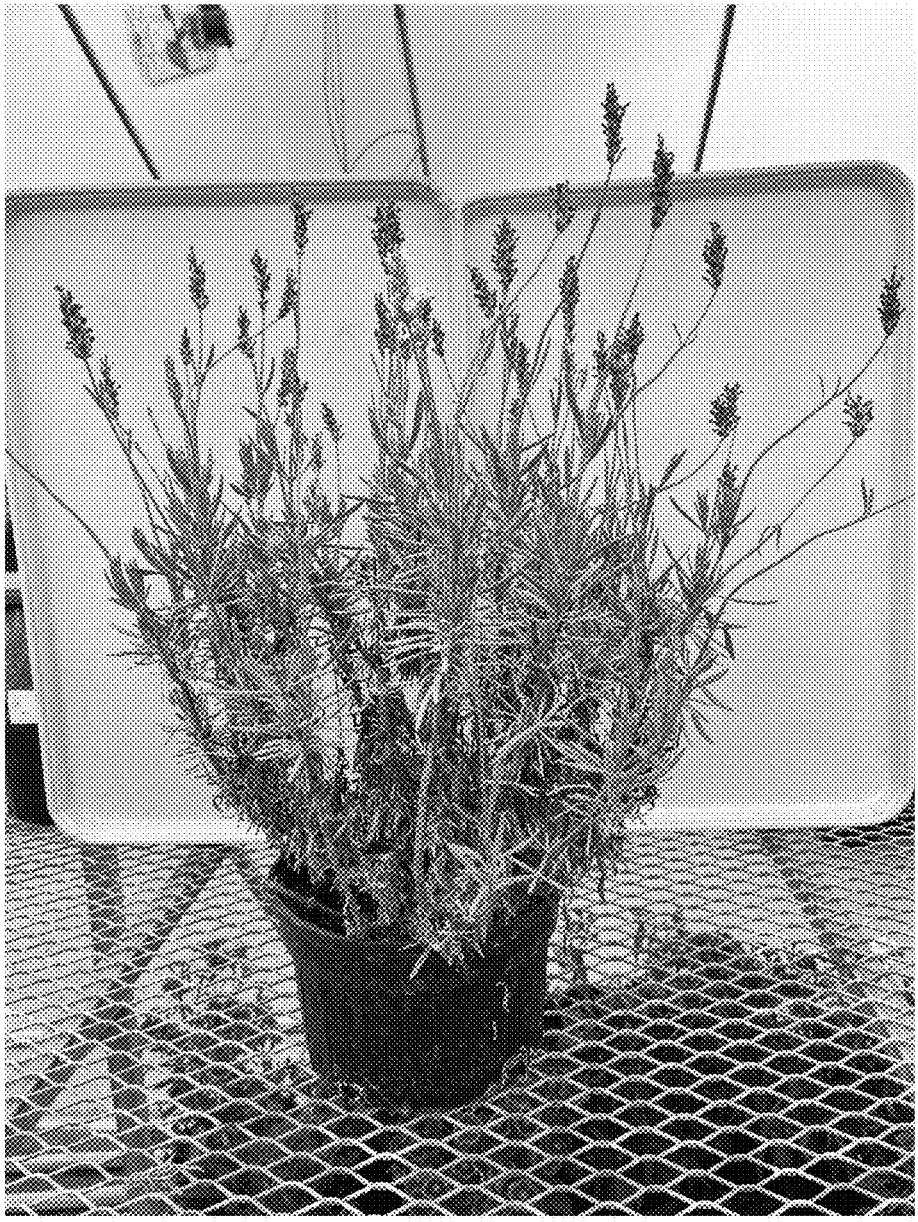

FIG. 2 illustrates in full color a typical plant of 'SENS-M1' grown in a greenhouse in Kintnersville, PA. Age of the plant photographed is approximately 9 months from a rooted cutting.

The photographs were taken using conventional techniques and although colors may appear different from actual colors due to light reflectance are as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SENS-M1' plants grown outdoors in Kintnersville, PA. Plants were vernalized at approximately 35° F. for 5 months. Plant age at description was approximately 9 months from an unrooted cutting. General light conditions are bright, normal sunlight. Measurements and numerical values represent averages of typical plant types.

Botanical classification: *Lavandula* x *intermediata* 'SENS-M1'.

PROPAGATION

Time to initiate roots: About 10 to 14 days at approximately 21° C.

Time to produce a rooted cutting: About 25 to 35 days at 21° C.

Root description: Well-branched woody main roots expending into fine, fibrous secondary roots. Older roots colored grey-Brown N199B. Younger roots colored Orange-White 159A.

PLANT

Age of plant described: Approximately 9 months from an unrooted cutting. 5 months of vernalization.

Plant height: 15 to 20 cm to the top of the foliar plane. 30 to 40 cm to the top of the flowering plane.

Plant spread: Approximately 25 cm.

Plant shape: Upright and rounded.

Growth rate: Moderate.

Plant habit: Dense, upright flowering perennial.

Stem:

*Shape*.—Quadrangular.

*Texture*.—Young stems; dull and short pubescent; mature wood is slightly scaly.

*Length*.—Average range 12 to 16 cm.

*Diameter*.—4 to 5 mm.

*Strength*.—Strong, non-brittle and difficult to break.

*Aspect*.—Upright and curved outward.

*Color*.—

*Juvenile color*.—Green 138B.

*Mature color*.—Greyed-Purple N186A streaked N187C and N187D.

Branching characteristics: An average of 8 to 10 lateral branches on a plant in a 4 inch container. 1 to 2 secondary branches develop on each of these to rebloom.

Internode length: Average range 1.2 to 2.0 cm.

FOLIAGE

Leaf:

*Arrangement*.—Opposite to slightly whorled.

*Leaf type*.—Simple.

*Quantity*.—Average 20 to 28 per 10 cm of branch.

*Average length*.—5 cm.

*Average width*.—1 cm.

*Depth*.—7 mm.

*Shape of blade*.—Narrow oblong to narrowly oblanceolate.

*Apex*.—Acute.

*Base*.—Cuneate.

*Attachment*.—Sessile.

*Margin*.—Entire.

*Texture of all surfaces*.—Puberulent.

*Leaf internode*.—1 to 15 mm. Very dense in upper sections, moderately dense base.

*Leaf fragrance*.—Strong lavender scent.

*Color*.—Young foliage upper side: RHS Greyed-Green 191B. Young foliage under side: Greyed-Green 191B. Mature foliage upper side: RHS Greyed-Green 191B flushed 192A. Mature foliage under side: Greyed-Green 191B flushed 192B.

*Venation*.—Type: Parallel. Venation color upper side: Indistinguishable from foliage color. Venation color under side: Indistinguishable from foliage color.

FLOWER

Bloom period: Blooms early to mid-June on the east coast of the United States. Continuously for 6 to 8 weeks, longer if side florets develop.

Inflorescence:

*Form*.—Small single flower in verticillasters arranged in cylindrical spikes. Infertile bracts not observed. Number of individual flowers per spike: Average 30 to 40. Whorls per spike: 6 to 10. Flowers per whorl: 4 to 6. Distance between whorls: Short (flowers weakly overlapping when open).

*Inflorescences quantity*.—1 per lateral branch with 1 to 3 subsequent inflorescences on secondary branches.

*Inflorescence lastingness*.—Average 12 weeks on the plant and as a fresh cut flower.

*Attitude of flowering stems at full bloom*.—Semi-erect.

*Fragrance*.—Floral, lavender scent. More floral than pungent herbaceous.

*Inflorescence size*.—Length: 4 to 6 cm. Width: 2 cm.

Individual flower:

*Corolla shape*.—Salverform Depth: About 10 mm. Diameter: About 5 mm. Throat Diameter: About 2 mm. Texture: Glabrous all surfaces. Tube Length: 4 mm. Tube Diameter: 2 mm. Tube Texture: Glabrous all surfaces. Tube Color: Exterior White N155B. Interior White N155A. Flower Lastingness: About 4 to 6 weeks.

Petals: Dull and smooth on upper and lower surfaces, rotate in arrangement, 2 (upper lip split in 2 lobes, lower lip split in 3 lobes; all lobes are identical in shape and color), spathulate in shape, lower 50% of petals are fused into tube, entire margin, upper part of petal apex split into two lobes, lower petal apex split into three lobes, apexes are rounded, upper lip is 5 mm in length and 6 mm in width, lower lip 3 mm in length and 7 mm in width.

*Petal coloration*.—Immature: White N155A, upper and lower surfaces. Mature: White N155B, upper and lower surfaces. Fading: White N155D, upper and lower surfaces.

Calyx:

*Calyx width*.—3 mm.

*Calyx length*.—5 mm.

*Calyx shape*.—Flattened tube.

*Texture*.—Short pubescence all surfaces.

*Calyx color*.—Exterior: Greyed-Green 191B. Interior: Greyed-Green 191C.

Bracts:

*Quantity*.—1 per individual flower.

*Bract shape*.—Deltoid.

*Bract apex*.—Acute.

*Margin*.—Entire.

*Base*.—Broadly tapered.

*Texture*.—Short pubescence all surfaces.

*Size*.—5 to 8 mm long and 3 to 5 mm in width.

*Bract color*.—Lower Surface: Greyed-Green 191C. Upper Surface: Greyed-Green 191B.

Bud:

*Length*.—6 mm.

*Diameter*.—3 mm.

*Shape*.—Ovate

*Color*.—White 155A.

*Rate of opening*.—Varies with climactic conditions; Approximately 1 week from colored bud to open flower.

Peduncle:

*Peduncle length*.—Average range 6.5 to 8 cm.

*Peduncle diameter*.—3 mm.

*Aspect*.—Straight.

*Strength*.—Very firm and strong.

*Color*.—RHS Green 138A.

*Texture*.—Ridged with short pubescence.

REPRODUCTIVE ORGANS

Gynoecium:

*Pistil length*.—5 mm.

*Stigma shape*.—Narrow, club-shaped.

*Stigma color*.—RHS White 155A.

*Style length*.—4 mm.

*Ovary color*.—RHS Greyed-Green 191C

Androecium:

*Stamen number*.—4.

*Filament length*.—2 mm.

*Filament color*.—RHS White N155D.

*Anther length*.—1 mm.

*Anther shape*.—Dorsifixed.

*Anther color*.—Orange White 159C

*Pollen color*.—Orange White 159B, scant.

OTHER CHARACTERISTICS

Seeds and fruits: Seed production not observed to date.

Disease/pest resistance: Has shown good resistance to leaf spot and root disease caused by *Phytophthora* sp., *Pythium* sp. and *Rhizoctonia* sp.

Temperature tolerance: USDA Zones 5-10.

What is claimed is:

1. A new and distinct cultivar of *Lavandula* plant named 'SENS-M1' as herein illustrated and described.

* * * * *